United States Patent [19]

Duhamel et al.

[11] Patent Number: 4,876,370

[45] Date of Patent: Oct. 24, 1989

[54] 1,3,5-NONATRIENE DERIVATIVES, THEIR PREPARATION AND THEIR USE

[75] Inventors: Lucette Duhamel; Pierre Duhamel, both of Mont Saint Aignan, France

[73] Assignee: Rhone-Poulenc Sante, Antony, France

[21] Appl. No.: 245,920

[22] Filed: Sep. 19, 1988

[30] Foreign Application Priority Data

Sep. 22, 1987 [FR] France .................. 87 13055

[51] Int. Cl.$^4$ .............. C07D 317/16; C07C 47/21; C07C 43/303

[52] U.S. Cl. .................. 549/455; 549/347; 549/369; 568/495; 568/596

[58] Field of Search .............. 549/455, 347, 369; 568/495, 596

[56] References Cited

U.S. PATENT DOCUMENTS

| | | | |
|---|---|---|---|
| 3,985,813 | 10/1926 | Labovitz | 568/596 |
| 4,087,465 | 5/1978 | Decor | 568/596 |
| 4,100,201 | 7/1978 | Decor | 568/596 |

*Primary Examiner*—Nicky Chan
*Attorney, Agent, or Firm*—Stevens, Davis, Miller & Mosher

[57] ABSTRACT

1,3,5-Nonatriene derivatives of formula:

1,3,5-Nonatriene derivatives of formula:

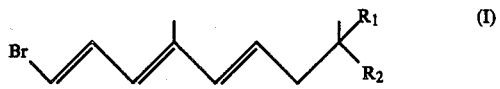

(I)

in which $R_1$ and $R_2$, together with the carbon atom to which they are linked, form a carbonyl group, or each of $R_1$ and $R_2$ denotes alkoxy or $R_1$ and $R_2$ together form an alkylenedioxy radical, which may be made by reaction of a butadiene derivative of formula:

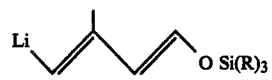

in which R is alkyl or phenyl, with a butanal ketoacetal of 10 formula:

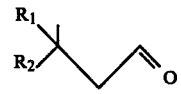

followed by reaction of the product with a halomethyltriphenylphosphonium halide, are useful intermediates e.g. for the production of phytol.

2 Claims, No Drawings

1,3,5-NONATRIENE DERIVATIVES, THEIR PREPARATION AND THEIR USE

The present invention provides a new 1,3,5-nonatriene derivative of the formula:

  (I)

in which either $R_1$ and $R_2$, together with the carbon atom to which they are linked, form a carbonyl group, or $R_1$ and $R_2$ each denote an alkoxy radical of 1 to 4 carbon atoms or $R_1$ and $R_2$ together form an alkylenedioxy radical, preferably derived from a vicinal diol of 2 to 4 carbon atoms, e.g. ethylene glycol.

According to a feature of the present invention, the compounds of formula (I) are prepared by reacting a 1,3-butadiene derivative of formula:

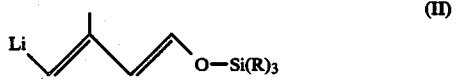  (II)

in which R denotes alkyl of 1 to 4 carbon atoms or phenyl, prepared preferably in situ by halogen-lithium exchange from the corresponding bromine compound with a butanal ketoacetal of formula:

  (III)

in which each of $R_1$ and $R_2$ denotes an alkoxy radical or together they form an alkylenedioxy radical, and then reacting the 3-methyl-7-oxo-2,4-octadienal oxoketal thus obtained with a halomethyltriphenylphosphonium halide.

The compound of formula (III) is generally added to the product of formula (II), prepared in situ by reaction with an organolithium derivative such as tert-butyllithium, at a temperature below −20° C., preferably below −50° C., the operation being carried out in an anhydrous organic solvent chosen from ethers such as ethyl ether or tetrahydrofuran and aliphatic or aromatic hydrocarbons. The 3-methyl-7-oxo-2,4-octadienal oxoketal is obtained after hydrolysis of the reaction mixture, e.g. in an acetic medium, the operation being generally carried out at a temperature of about 20° C.

The reaction of the halomethyltriphenylphosphonium halide such as bromomethyltriphenylphosphonium bromide with the 3-methyl-7-oxo-2,4-octadienal oxoketal is generally carried out in the presence of a metal alcoholate such as potassium tert-butylate in an anhydrous organic solvent such as tetrahydrofuran.

The 1-bromo-2-methyl-4-trialkylsilyloxy-1,3-butadiene precursor of the product of formula (II) can be obtained by reaction of a halotrialkylsilane, such as chlorotrimethylsilane or bromotrimethylsilane, with 4-bromo-3-methyl-2-butenal, the operation being carried out in an organic solvent such as pentane and acetonitrile in the presence of an organic base such as triethylamine, at a temperature in the region of 20° C.

4-Bromo-3-methyl-2-butenal can be obtained by reaction of N-bromosuccinimide with a 3-methyl-1-trialkylsilyloxybutadiene in aqueous alcoholic medium at a temperature below −10° C., followed by hydrolysis in an acidic medium.

3-Methyl-1-trialkylsilyloxybutadienes can be obtained by reaction of halotrialkylsilanes with prenal, in an organic solvent such as ethyl ether in the presence of an organic base such as triethylamine.

The product of general formula (III) can be obtained by acetalization of the ketone group of ethyl acetylacetate, followed by the reduction of the acetal obtained to alcohol by means of, for example, lithium aluminium hydride, followed by oxidation of the alcohol to a ketoketal aldehyde of formula (III), for example by means of the $CrO_3$-pyridine mixture.

The products of general formula (I) are intermediates which are particularly useful in terpene synthesis.

For example, the products of general formula (I) can be condensed with methylheptenone (i.e. 6-methylhept-5-en-2-one) to produce the acetal of 10-hydroxy-6,10,14-trimethyl-4,6,8,13-pentadecatetraen-2-one, which, after hydrolysis, dehydration and reduction, gives 6,10,14-trimethyl-2-pentadecanone which, after condensation with trimethylsilylvinyllithium, gives 3,7,11,15-tetramethyl-2-hexadecenal which, after reduction, gives phytol which, by condensation with trimethylhydroquinone, enables vitamin E to be obtained.

The condensation of a product of general formula (I) with methylheptenone is carried out under the conditions described above for the condensation of a product of general formula (III) with a product of general formula (II) after a halogen-metal exchange reaction.

The dehydration and the hydrolysis of the hydroxyacetal thus obtained are performed by heating in a hydroacetonic medium in an acidic medium.

The following examples illustrate the invention.

EXAMPLE 1

Anhydrous ethyl ether (11 cc) and 1-bromo-2-methyl-4-trimethylsilyloxy-1,3-butadiene (0.9 g) are introduced under an argon atmosphere into a 50-cc round-bottomed flask. This is cooled to −70° C. and then a solution (3.25 cc) of 1.65M tert-butyllithium in pentane is added over 10 minutes. The mixture is stirred at −70° C. for 100 minutes and 3,3-ethylenedioxybutanal (0.4 g) is then added in solution in anhydrous ethyl ether (4 cc). The temperature is allowed to rise to −30° C. and stirring is performed for 30 minutes. Further stirring is performed for 20 minutes at −20° C. and then the mixture is cooled to −60° C. N Hydrochloric acid (11.5 cc) is added over 20 minutes. The temperature is allowed to rise to about 20° C. After the reaction mixture has been taken up with ether and water and the organic phases have been dried over magnesium sulphate, and after flash chromatography, 7,7-ethylenedioxy-3-methyl-2,4-octadienal (0.33 g) is obtained, its characteristics being as follows:

Proton nuclear magnetic resonance spectrum (60 MHz; $CCl_4$; chemical shifts in ppm; coupling constants in Hz): 10 (d, 1H, 8.5 Hz); 6.2 (m, 2H); 5.8 (d, 1H, 8.5 Hz); 3.9 (s, 4H); 2.4 (d, 2H, 3.3 Hz); 2.2 (s, 2.4H); 2.0 (s, 0.6H); 1.1 (s, 3H).

Infrared spectrum: 2960, 1665, 1595, 1380, 1205, 1120 and 1050 $cm^{-1}$.

The yield is 55%.

The ratio of the forms E/Z is 80/20.

Anhydrous tetrahydrofuran (22 cc) and bromomethyltriphenylphosphonium bromide (1.7 g, 3.9 mmol) are introduced into a 50-cc round-bottomed flask. This is cooled to −70° C. and potassium tert-butylate (0.44 g) is then added over 10 minutes. The mixture is stirred for 1 hour 30 minutes and 7,7-ethylenedioxy-3-methyl-2,4-octadienal (0.5 g) is then added in solution in tetrahydrofuran (3 cc) over 10 minutes. The temperature is allowed to rise to 10° C. and stirring is then performed for 2 hours 20 minutes. Water (12 cc) is quickly added and stirring is then performed for 15 minutes. After extraction, the organic phases are dried over magnesium sulphate. After evaporation of the solvents, the product obtained is placed in a mortar and is taken up with petroleum ether; the triphenylphosphine oxide which precipitates is ground until white and is then separated by filtration. After evaporation of the petroleum ether, 8,8-ethylenedioxy-1-bromo-4-methyl-1,3,5-nonatriene (0.49 g) is obtained, its characteristics being as follows:

Proton nuclear magnetic resonance spectrum (60 MHz; CCl$_4$): 5.4–6.6 (m, 5H); 3.95 (s, 4H); 2.45 (d, 2H, 6.4 Hz); 1.85 (s, 3H); 1.25 (s, 3H).

Infrared spectrum (film): 2980, 1445, 1380, 1105 and 1050 cm$^{-1}$.

The yield is 70%.

1-Bromo-2-methyl-4-trimethylsilyloxybutadiene can be prepared as follows:

Pentane (120 cc), acetonitrile (120 cc), 4-bromo-3-methyl-2-butenal (9 g, 107 mmol) and triethylamine (13 g) are introduced under an argon atmosphere into a 500-cc three-necked round-bottomed flask. The temperature is kept at 0° C. and bromotrimethylsilane (19.6 g) is then added over 20 minutes. The mixture is stirred for 2 days at a temperature in the region of 20° C. The pentane solution is sampled with a syringe and is then replaced with an equivalent quantity of pentane. The operation is repeated 4 times. The various pentane solutions are combined and the pentane is removed, any entry of air being excluded. The residue obtained is purified by distillation. 1-Bromo-2-methyl-4-trimethylsilyloxybutadiene (6.5 g) is thus obtained (B.P.$_{0.25}$=59° C.).

The yield is 50%.

4-Bromo-3-methyl-2-butenal can be prepared as follows:

3-Methyl-1-trimethylsilyloxybutadiene (8 g, 51.2 mmol) is added quickly to a mixture of methanol (160 cc) and water (16 cc) maintained at 0° C., followed immediately by finely pulverized N-bromosuccinimide (9.12 g) over 25 minutes, while the temperature is kept below 5° C. The mixture is stirred for 15 minutes at 3° C. and then the methanol is evaporated off. The residue is taken up with petroleum ether (150 cc, then 2×50 cc). The petroleum ether is evaporated off and the residue is then taken up with ethyl ether (200 cc). N hydrochloric acid (15 cc) is added and the mixture is stirred for 30 minutes at 3° C. After extraction, drying of the organic phases over magnesium sulphate and evaporation of the solvents, 4-bromo-3-methyl-2-butenal (7.1 g) is obtained in an 85% yield.

3-Methyl-1-trimethylsilyloxybutadiene can be prepared as follows:

Anhydrous ethyl ether (70 cc), distilled prenal (35 g, 0.42 mole), distilled triethylamine (45 g) and zinc chloride (0.5 g) dried over phosphoric anhydride are introduced under an argon atmosphere into a 250-cc round-bottomed flask. Chlorotrimethylsilane (57 cc) is added over 30 minutes. The mixture is heated under reflux for 25 hours. After cooling, pentane (75 cc) is added and the mixture is stirred for 15 minutes. Triethylamine hydrochloride is separated off by filtration and is washed with pentane (300 cc). After evaporation of the solvents, the residue is distilled. 3-Methyl-1-trimethylsilyloxybutadiene (50 g) is thus obtained (B.P.$_{13}$=43° C.).

The yield is 77%.

3,3-Ethylenedioxybutanal can be prepared as follows:

Pyridine (7.2 g) and chromic oxide (CrO$_3$) (4.6 g) are added in small fractions to dichloromethane (150 cc) over 10 minutes. After 15 minutes' stirring at a temperature in the region of 20° C., 2,2-ethylenedioxy-4-hydroxybutane (0.85 g, 6.4 mmol) is added quickly as a solution in dichloromethane (2 cc). After 15 minutes' stirring at 20° C., the black, viscous precipitate is separated off by filtration through silica and is washed with ether. After evaporation of the solvents, 3,3-ethylenedioxybutanal (0.59 g) is obtained (B.P.$_{0.4}$=35° C.).

The yield is 70%.

2,2-Ethylenedioxy-4-hydroxybutane can be prepared as follows:

Lithium aluminium hydride (2 g, 51 mmol) is added in small portions to anhydrous ethyl ether (200 cc). The mixture is cooled to 0° C. and ethyl 3,3-ethylenedioxybutanoate (3 g, 17 mmol) is then added over 10 minutes as a solution in anhydrous ethyl ether (10 cc). The mixture is stirred for 2 hours 30 minutes at a temperature in the region of 20° C. and is then hydrolysed by adding a saturated sodium sulphate solution (12 cc). After 2 hours the white precipitate is separated off by filtration. The organic phases are dried over magnesium sulphate. 2,2-Ethylenedioxy-4-hydroxybutane (2.22 g) is thus obtained.

The yield is 97%.

Ethyl 3,3-ethylenedioxybutanoate can be prepared as follows:

Benzene (50 cc), ethyl acetylacetate (30 g, 231 mmol) and ethylene glycol (16 g), followed by p-toluenesulphonic acid (0.5 g), are introduced into a round-bottomed flask fitted with a Dean and Stark apparatus. The mixture is heated under reflux while the azeotrope is distilled off for 2 hours 30 minutes. After the removal of benzene, ethyl 3,3-ethylenedioxybutanoate (37 g) is obtained (B.P.$_{12}$=98° C.).

The yield is 90%.

EXAMPLE 2

8,8-Ethylenedioxy-1-bromo-4-methyl-1,3,5-nonatriene (0.3 g, 1 mmol) is introduced under an argon atmosphere into ethyl ether (8 cc) and the mixture is cooled to −70° C. A 1.65M solution of tert-butyllithium in pentane (1.2 cc) is added over 10 minutes. Stirring is performed for 1 hour 50 minutes and 6-methylhept-5-en-2-one (0.1 g) is then added over 10 minutes as a solution in anhydrous ethyl ester (3 cc). The temperature is allowed to rise to about 20° C. over 1 hour and stirring is then continued for 25 minutes. The mixture is cooled to −10° C. and a 5% strength solution of sodium bicarbonate (2.66 cc) is then added. After extraction with ethyl ether and drying of the organic phases over the magnesium sulphate, followed by flash chromatography, 2,2-ethylenedoxy-10-hydroxy-6,10,14-trimethyl-4,6,8,13-pentadecatetraene (0.15 g) is obtained in a 58% yield, its characteristics being as follows:

Proton nuclear magnetic resonance spectrum (60 MHz; CDCl$_3$): 5.3–7 (m 5H); 5.1 (t, 1H, 6.5 Hz); 3.95 (s, 4H); 2.43 (d, 2H, 7.2 Hz); 2.05 (m, 1H); 1.05–1.95 (m, 19H).

Infrared spectrum (film): 3495, 2930, 1450, 1375, 1105 and 1050 cm$^{-1}$.

The hydroxyacetal obtained above (0.11 g) is refluxed for 3 minutes in acetone (5 cc). N hydrochloric acid (0.55 cc) is then added and refluxing is continued for 20 minutes. After cooling, the reaction mixture is poured into a 5% strength aqueous sodium carbonate solution (30 cc). After extracting with ether, drying the organic phases over magnesium sulphate and evaporating the solvents, 6,10,14-trimethyl-3,5,7,9,13-pentadecaen-2-one (0.08 g) is obtained.

The yield is 90%.

Ethanol (20 cc), 6,10,14-trimethyl-3,5,7,9,13-pentadecaen-2-one (0.4 g) and palladium on charcoal (0.2 g) containing 5% by weight of palladium are introduced into a 100-cc round-bottomed flask. This is purged with argon and is then placed under a hydrogen atmosphere. After 2 hours' stirring at a temperature in the region of 20° C., the catalyst is separated off by filtration and is washed with ethanol. After concentrating the ethanolic phases to dryness, 6,10,14-trimethyl-2-pentadecanone (0.35 g) is obtained, and is characterized by its infrared spectrum and its proton nuclear magnetic resonance spectrum.

The yield is 85%.

1-Bromo-2-trimethylsilyloxyethylene (1 g, 5.3 mmol) in anhydrous ethyl ether (10 cc) is introduced under an argon atmosphere into a 50-cc round-bottomed flask. The mixture is cooled to −70° C. and a 1.2M solution (8 cc) of tert-butyllitium in pentane is then added. Stirring is performed for 90 minutes at −70° C. and then 6,10,14-trimethyl-2-pentadecanone (1.19 g) is added in solution in anhydrous ethyl ether (3 cc). The temperature is allowed to rise to about −15° C. and stirring is continued for 1 hour. The solution is cooled to −60° C. and 3N hydrochloric acid (7 cc) is then added over 15 minutes. Stirring is performed for 30 minutes at 10° C. After extracting with ether, washing the ether phases until neutral, drying the ether phases over magnesium sulphate, filtering and evaporating off the solvents, a product is obtained and is purified by flash chromatography. 3,7,11,15-Tetramethyl-2-hexadecenal (1.05 g) is thus obtained and is characterized by its infrared spectrum and its proton nuclear magnetic resonance spectrum.

The yield is 80%.

Lithium aluminium hydride (0.15 g, 1 mmol) is introduced over 5 minutes into a round-bottomed flask containing anhydrous ether (50 cc) at 0° C. The mixture is stirred for 10 minutes and 3,7,11,15-tetramethyl-2-hexadecenal (0.3 g, 1 mmol) is then added in solution in anhydrous ethyl ether (5 cc). The mixture is stirred for 1 hour at 0° C. and ethyl acetate (3 cc) and water (7 cc) saturated with ammonium chloride are then added. The mixture is stirred for 15 minutes and is then extracted with ethyl ether. The organic phases are dried over magnesium sulphate. After filtering and evaporating off the solvents, 3,7,11,15-tetramethyl-2-hexadecenol (or phytol) is obtained and is characterized by its infrared spectrum and its proton nuclear magnetic resonance spectrum.

We claim:

1. A 1,3,5-nonatriene derivative of the formula:

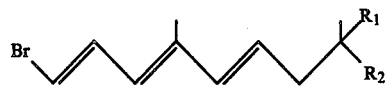

in which either $R_1$ and $R_2$, together with the carbon atom to which they are linked, form a carbonyl group or $R_1$ and $R_2$ each denote an alkoxy radical of 1 to 4 carbon atoms or $R_1$ and $R_2$ together form an alkylenedioxy radical.

2. A 1,3,5-nonatriene derivative according to claim 1 which is 8,8-ethylenedioxy-1-bromo-4-methyl-1,3,5-nonatriene.

* * * * *